(12) United States Patent
Wiedrich et al.

(10) Patent No.: US 9,681,869 B2
(45) Date of Patent: Jun. 20, 2017

(54) BIOSTAPLES SUITABLE FOR WRIST, HAND AND OTHER LIGAMENT REPLACEMENTS OR REPAIRS

(75) Inventors: Thomas Wiedrich, Wilmette, IL (US); Tian Davis, Ruskin, FL (US); Thomas J. Koob, Tampa, FL (US)

(73) Assignee: MiMedx Group, Inc., Marietta, GA (US)

(*) Notice: Subject to any disclaimer, the term of this patent is extended or adjusted under 35 U.S.C. 154(b) by 1426 days.

(21) Appl. No.: 12/389,696

(22) Filed: Feb. 20, 2009

(65) Prior Publication Data

US 2009/0216233 A1 Aug. 27, 2009

Related U.S. Application Data

(60) Provisional application No. 61/030,768, filed on Feb. 22, 2008.

(51) Int. Cl.
*A61B 17/06* (2006.01)
*A61B 17/064* (2006.01)
*A61L 31/04* (2006.01)
*A61B 17/00* (2006.01)

(52) U.S. Cl.
CPC ........ *A61B 17/064* (2013.01); *A61B 17/0642* (2013.01); *A61L 31/044* (2013.01); *A61B 2017/00004* (2013.01); *A61B 2017/00084* (2013.01); *A61B 2017/00526* (2013.01)

(58) Field of Classification Search
CPC .................................................. A61B 17/064
USPC ................ 606/75, 330–331; 623/13.11–13.2
See application file for complete search history.

(56) References Cited

U.S. PATENT DOCUMENTS

| | | | |
|---|---|---|---|
| 3,316,699 A | | 5/1967 | Mattingly |
| 3,973,277 A | * | 8/1976 | Semple et al. ............. 623/13.14 |
| 4,414,967 A | * | 11/1983 | Shapiro ........................... 606/75 |
| 4,570,623 A | * | 2/1986 | Ellison et al. .................. 606/75 |
| 4,590,928 A | | 5/1986 | Hunt et al. |
| 4,792,336 A | | 12/1988 | Hlavacek et al. |
| 4,841,962 A | | 6/1989 | Berg et al. |
| 4,883,486 A | | 11/1989 | Kapadia et al. |
| 4,979,956 A | | 12/1990 | Silvestrini |
| 5,053,038 A | * | 10/1991 | Sheehan ......................... 606/75 |
| 5,078,744 A | * | 1/1992 | Chvapil ..................... 606/86 R |

(Continued)

FOREIGN PATENT DOCUMENTS

| | | |
|---|---|---|
| CA | 2285161 | 4/2001 |
| EP | 0 943 346 A1 | 9/1999 |

(Continued)

OTHER PUBLICATIONS

Brunelli et al., Slip-knot flexor tendon suture in zone II allowing immediate mobilisation, The Hand, 1983, vol. 15, pp. 352-358.

(Continued)

*Primary Examiner* — Andrew Yang
(74) *Attorney, Agent, or Firm* — Myers Bigel, P.A.

(57) ABSTRACT

The disclosure describes implantable medical products, that include dry or partially hydrated biocompatible biostaples suitable for ligament repairs or replacements comprising collagen fibers that may be configured to expand in situ after implantation to frictionally engage a bone tunnel wall or bone sleeve to thereby affix the construct in the bone tunnel.

11 Claims, 16 Drawing Sheets

(56) References Cited

U.S. PATENT DOCUMENTS

| | | | |
|---|---|---|---|
| 5,106,949 A | 4/1992 | Kemp et al. | |
| 5,190,057 A | 3/1993 | Sarfarazi | |
| 5,256,418 A | 10/1993 | Kemp et al. | |
| 5,258,009 A * | 11/1993 | Conners | 606/219 |
| 5,263,984 A * | 11/1993 | Li et al. | 623/13.18 |
| 5,350,400 A * | 9/1994 | Esposito et al. | 606/219 |
| 5,378,469 A | 1/1995 | Kemp et al. | |
| 5,656,605 A | 8/1997 | Hansson et al. | |
| 5,713,374 A | 2/1998 | Pachence et al. | |
| 5,718,012 A | 2/1998 | Cavallaro | |
| 5,718,717 A | 2/1998 | Bonutti | |
| 6,090,117 A | 7/2000 | Shimizu | |
| 6,224,630 B1 | 5/2001 | Bao et al. | |
| 6,277,397 B1 | 8/2001 | Shimizu | |
| 6,280,474 B1 | 8/2001 | Cassidy et al. | |
| 6,292,697 B1 | 9/2001 | Roberts | |
| 6,335,007 B1 | 1/2002 | Shimizu et al. | |
| 6,531,147 B2 | 3/2003 | Sawhney et al. | |
| 6,565,960 B2 | 5/2003 | Koob et al. | |
| 6,589,257 B1 | 7/2003 | Shimizu | |
| 6,592,623 B1 | 7/2003 | Bowlin et al. | |
| 6,645,247 B2 | 11/2003 | Ferree | |
| 6,692,528 B2 | 2/2004 | Ward et al. | |
| 6,713,537 B1 | 3/2004 | Ueda et al. | |
| 6,730,124 B2 | 5/2004 | Steiner | |
| 6,752,831 B2 | 6/2004 | Sybert et al. | |
| 6,821,530 B2 | 11/2004 | Koob et al. | |
| 6,936,072 B2 | 8/2005 | Lambrecht et al. | |
| 6,955,683 B2 | 10/2005 | Bonutti | |
| 7,084,082 B1 | 8/2006 | Shimizu | |
| 7,090,690 B2 | 8/2006 | Foerster et al. | |
| 7,115,146 B2 | 10/2006 | Boyer, II et al. | |
| 7,135,040 B2 | 11/2006 | Wang et al. | |
| 7,309,359 B2 | 12/2007 | Trieu et al. | |
| 7,354,627 B2 | 4/2008 | Pedrozo et al. | |
| 2001/0018619 A1 | 8/2001 | Enzerink et al. | |
| 2002/0037940 A1* | 3/2002 | Koob et al. | 521/55 |
| 2002/0090725 A1 | 7/2002 | Simpson et al. | |
| 2002/0123805 A1 | 9/2002 | Murray et al. | |
| 2003/0100108 A1 | 5/2003 | Altman et al. | |
| 2003/0230316 A1 | 12/2003 | Glucksman et al. | |
| 2004/0110439 A1 | 6/2004 | Chaikof et al. | |
| 2004/0131562 A1 | 7/2004 | Gower et al. | |
| 2004/0193241 A1 | 9/2004 | Stinson | |
| 2004/0224406 A1 | 11/2004 | Altman et al. | |
| 2004/0267362 A1 | 12/2004 | Hwang et al. | |
| 2005/0080454 A1* | 4/2005 | Drews | A61B 17/064 606/221 |
| 2006/0095134 A1 | 5/2006 | Trieu et al. | |
| 2006/0257377 A1 | 11/2006 | Atala et al. | |
| 2006/0263417 A1 | 11/2006 | Lelkes et al. | |
| 2007/0118217 A1 | 5/2007 | Brulez et al. | |
| 2007/0248643 A1 | 10/2007 | Devore et al. | |
| 2008/0020012 A1 | 1/2008 | Ju et al. | |
| 2008/0038352 A1 | 2/2008 | Simpson et al. | |
| 2008/0124371 A1* | 5/2008 | Turos et al. | 424/422 |
| 2008/0161917 A1 | 7/2008 | Koob et al. | |
| 2008/0188933 A1 | 8/2008 | Koob et al. | |
| 2008/0200992 A1* | 8/2008 | Koob et al. | 623/23.72 |
| 2008/0215150 A1 | 9/2008 | Koob et al. | |
| 2009/0287308 A1 | 11/2009 | Davis et al. | |

FOREIGN PATENT DOCUMENTS

| | | |
|---|---|---|
| EP | 1493404 | 1/2005 |
| JP | 60-25213 | 7/1985 |
| JP | 09047457 | 2/1997 |
| WO | WO 96-14095 | 5/1996 |
| WO | WO 01-72241 | 10/2001 |
| WO | WO 03/007839 A2 | 1/2003 |
| WO | WO 2008-041183 | 4/2008 |

OTHER PUBLICATIONS

Greis et al, The influence of tendon length and fit on the strength of the tendon-bone tunnel complex, Am. J. Sports Med., 2001, 29:493-497.

Becker et al., Early active motion following a beveled technique of flexor tendon repair: Report on fifty cases, Journal of Hand Surgery, 1979, vol. 4 No. 5, pp. 454-460.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2002, 24:1285-1292.

Koob et al., Biocompatibility of NDGA-polymerized collagen fibers. I. Evaluation of cytotoxicity with tendon fibroblasts in vitro, © 2001John Wiley & Sons, Inc.

Koob et al., Biocompatibility of NDGA-polymerized collagen fibers. II. Attachment, proliferation, and migration of tendon fibroblasts in vitro, © 2001John Wiley & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Messina, The double armed suture: Tendon repair with immediate mobilization of the fingers, Journal of Hand Surgery, 1992, 17A:137-142.

Nottage et al., Arthroscopic Knot Tying Techniques, Arthroscopy: The Journal of Arthroscopic & Related Surgery 15(1999): 515-521.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British Volume,1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

Product advertisement, Conair QB3ECS Quick Braid Styling Kit, © 2007 (1 page).

Integra™ NeuraGen™ Nerve Guide, Product Broacher, 4 pages 2005.

Integra™ NeuraGen™ Nerve Guide, Product Webpage, http://www.integra-Is.com/products?product=88, Date unknown but believed to be prior to the filing date of the present application, 2 pages.

Integra™ NeuraWrap™ Nerve Protector, Product Webpage, http://www.integra-Is.com/products/?product=198, Date unknown but believed to be prior to the filing date of the present application, 2 pages.

Koob, Thomas, Biomimetic approaches to Tendon Repair, Comp. Biochem. and Physiol. A Mol. Integr. Phys., 133, 2002, p. 1171-1192.

International Search Report and Written Opinion for corresponding PCT application No. PCT/US2009/001087, Date of mailing Oct. 12, 2009.

Translation of Reference Excerpts serving as a concise statement of relevance for Japanese Examined Utility Model Application Publication No. 60-025213, published Jul. 27, 1985, 2 pages.

* cited by examiner

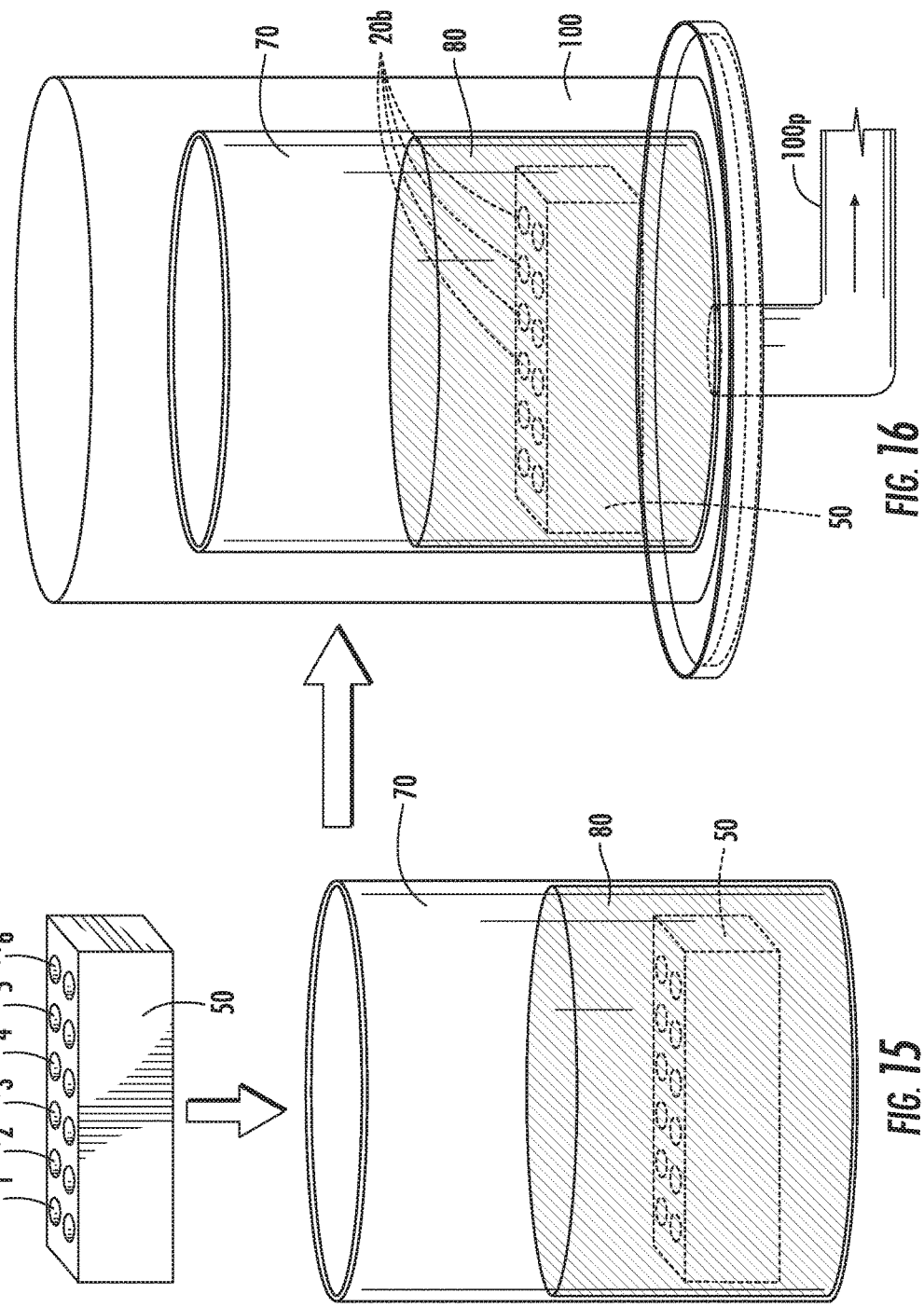

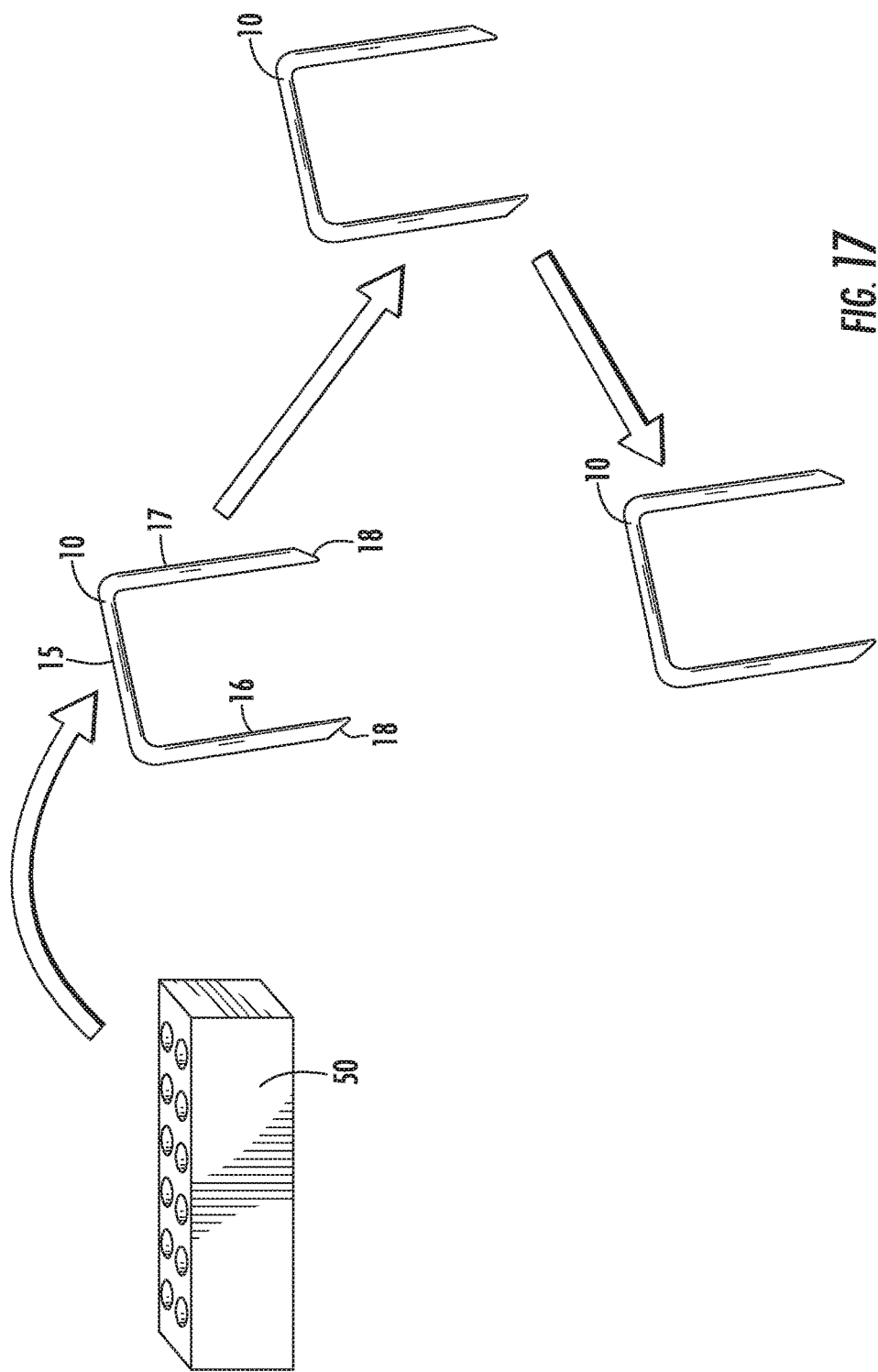

BIOSTAPLES SUITABLE FOR WRIST, HAND AND OTHER LIGAMENT REPLACEMENTS OR REPAIRS

RELATED APPLICATION

This application claims the benefit of priority of U.S. Provisional Application Ser. No. 61/030,768, filed Feb. 22, 2008, the contents of which are hereby incorporated by reference as if recited in full herein.

FIELD OF THE INVENTION

The invention relates to implantable medical constructs.

BACKGROUND OF THE INVENTION

The use of an implanted internal prosthetic device to repair or replace dysfunctional tissues in the skeletal system poses complex biomechanical challenges. One challenge is achieving a mechanically competent fixation of the device to the biological tissue at the reconstruction site. Fixation strength should be adequate to withstand loads encountered in vivo during the immediate post-operative period as well as during long-term progressive rehabilitation. Post-operative loads are generally managed by immobilization protocols in order to allow fixation strength to develop coordinately with the repair process. Rehabilitative loads are typically applied once the repaired structure attains sufficient mechanical competence. An effective fixation strategy should be able to achieve rapid fixation during the surgical procedure to maintain the proper positioning during the repair phase

SUMMARY OF EMBODIMENTS OF THE INVENTION

Embodiments of the present invention are directed to a medical construct of collagen fibers having a crown and two opposing legs forming a collagenous biocompatible staple (biostaple). Such biostaples can be used for any ligament repair/replacement in a wrist or hand, such as for example, any collateral ligament. Some particular embodiments of the present invention may be particularly suitable for scapholunate ligament repair or replacement and/or medial collateral ligament repair or replacement.

Some embodiments are directed to biostaples that include a biocompatible construct of collagen fibers having a crown and two opposing legs. The legs may be configured to frictionally engage a respective bone tunnel wall or bone sleeve to thereby affix the construct in position.

The collagen fibers can be arranged in an array of substantially parallel polymerized collagen fibers. The collagen fibers may comprise nordihydroguaiaretic acid (NDGA) polymerized collagen fibers. The legs of the dry or partially hydrated construct can have a cross-sectional area that is between about 80-99% that of the corresponding bone tunnel before implantation.

In some embodiments, the array of substantially parallel fibers include between about 10-200 elongate fibers compressed together so that adjacent fibers snugly contact each other. The fibers may optionally be held together using a gelatin material, such as, for example, an NDGA treated gelatin.

Yet other embodiments are directed to medical kits that include: (a) an implantable construct having a crown with opposing end portions that merge into a respective downwardly extending leg, the construct comprising collagen fibers and having sufficient rigidity to substantially retain its shape ex vivo and in vivo; and (b) a sterile package sealably enclosing the construct therein.

Still other embodiments are directed to methods of making a medical construct. The methods include: (a) gathering a plurality of loose elongate collagen fibers into a bundle; and (b) forming the collagen fibers into a construct having a crown and two opposing downwardly extending legs with sufficient rigidity to substantially retain its shape before and after implantation.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 15 is an exploded schematic view of a mold holding a plurality of fiber bundles in tunnels therein ready for insertion into a liquid bath according to embodiments of the present invention.

FIG. 16 illustrates the mold with the fiber bundles in the liquid bath shown in FIG. 15 and inside a vacuum system according to embodiments of the present invention.

FIG. 17 is a schematic illustration of the mold with the fibers after processing the fibers to have sufficient rigidity and adhesion so as to retain the staple shape according to embodiments of the present invention.

DETAILED DESCRIPTION

Figure 1:
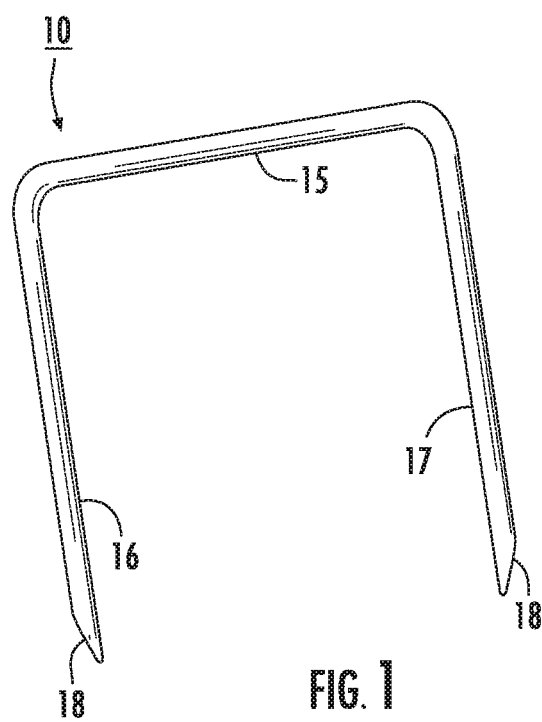
FIG. 1 is a front view of an exemplary biostaple according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Embodiments of the invention are particularly suitable for human or veterinary use.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" are used interchangeably herein to designate a product configured to repair or replace (at least a portion of) a natural tendon, ligament or other tissue of a mammalian subject (for veterinary or medical (human) applications). The term "implantable" means the so-noted device can be inserted, embedded, grafted or otherwise chronically attached or placed on or in a patient. The term "tissue" means skin, muscle, bone or other group of cells.

The term "array" means an arrangement of fibers in rows and/or columns, typically with respective fibers held close together in an elongate longitudinal (e.g., substantially parallel) orientation that are held together as in a matrix. The term "flexible" means that the so-called member can be flexed or bent without fracturing.

The term "biostaple" means a biocompatible, geometrically-shaped construct having a crown and two downwardly extending legs. The term "crown" refers to a top portion of the staple that spans or bridges between the legs. The biostaple can have a general or substantial "U" shape. The term "thread" refers to one or more strands, fibers or filaments of natural or synthetic material and includes sutures, wires, cords and the like.

The term "dry" means the construct has a moisture content substantially less than the amount present when fully hydrated. The term "partially hydrated" means that the construct and/or fibers thereof have a moisture content that is less than about 50%, typically less than about 75% of the moisture content at full hydration, measured ex vivo after 24 hours in a saline bath at ambient conditions.

The collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable mammalian donor, marine animal collagen such as echinoderms, molecularly engineered collagen, or gelatin (e.g., in any suitable form including solid, gel, hydrogels, liquids, or foams). In addition, the collagen can be digested with a protease before the oxidizing and polymerizing steps. The collagen can be in the form of microfibrils, fibrils, natural fibers, or synthetic fibers. Collagen "microfibrils," "fibrils," "fibers," and "natural fibers" refer to naturally-occurring structures found in a tendon. Microfibrils are about 3.5 to 50 nm in diameter. Fibrils are about 50 nm to 50 µm in diameter. Natural fibers are above 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber.

Of course, synthetic collagen fibers can include non-collagenous components, such as particulates, hydroxyapatite and other mineral phases, or drugs that facilitate tissue growth. For example, the compositions can contain carbon nano-tubes, zinc nano-wires, nano-crystalline diamond, or other nano-scale particulates; larger crystalline and non-crystalline particulates such as calcium phosphate, calcium sulfate, and apatite minerals. For example, the compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, and decorin. See, e.g., U.S. Pat. No. 6,821,530, the contents of which are hereby incorporated by reference as if recited herein. In some embodiments, the constructs (e.g., staples) can contain cells, engineered cells, stem cells, and the like. Combinations of the above or other materials can be embedded, coated and/or otherwise attached to the construct.

Figure 2:
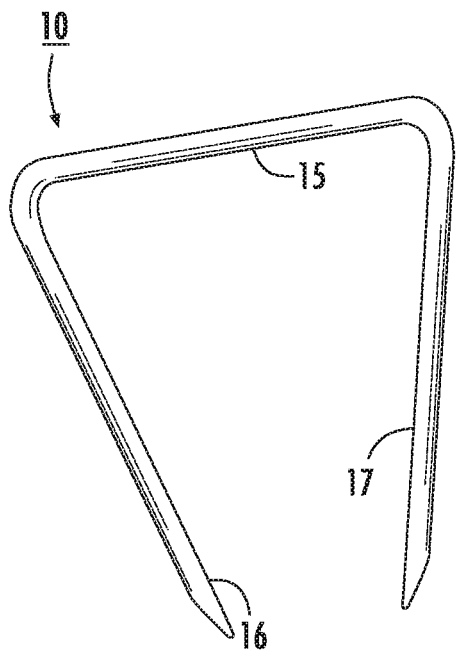
FIGS. 2 and 3 are front schematic views of other exemplary embodiments of a biostaple according to embodiments of the present invention.
Figure 3:
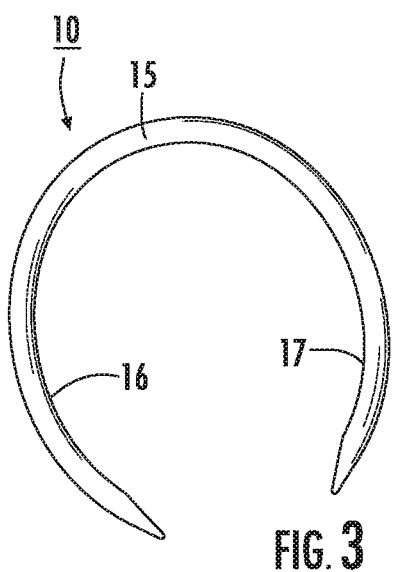

FIGS. 1-3 illustrate examples of biostaples 10 with a crown 15 and two downwardly extending spaced apart opposing legs 16, 17. In some embodiments, as shown in FIG. 1, the legs 16, 17 terminate into tapered or sharply angled leading edges 18. FIGS. 1-3 illustrate that the staple 10 can have a unitary body. FIG. 1 also illustrates that the staple 10 can have a substantially horizontal crown 15 with rounded opposing outer edge portions and that the legs 16, 17 can extend substantially orthogonal to the crown 15. FIG. 2 illustrates that the legs 16, 17 can angle inwardly from the outer edge portions of the crown 15. FIG. 3 illustrates that the staple 10 can be curvilinear, e.g., the crown 15 and legs 16, 17 define a substantially arcuate shape. Typically, as shown, the staple 10 has an open bottom so that the legs 16, 17 are spaced apart. The legs 16, 17 are shown has having substantially the same length and a substantially constant cross-sectional size. However, the legs 16, 17 may have different lengths such that one is shorter than another and each leg 16, 17 and/or the crown 15 can have a different cross-sectional size or shape. Typically, the staple legs 16, 17 can have a substantially circular cross section (FIG. 7B), but other shapes may be used. Examples of alternate geometric shapes include substantially rectangular, square, triangular and the like. The circular cross sectional shape may be particularly suitable for bone tunnels 110 (FIG. 7A) drilled into target bone with a relatively precise diameter.

Figure 4:
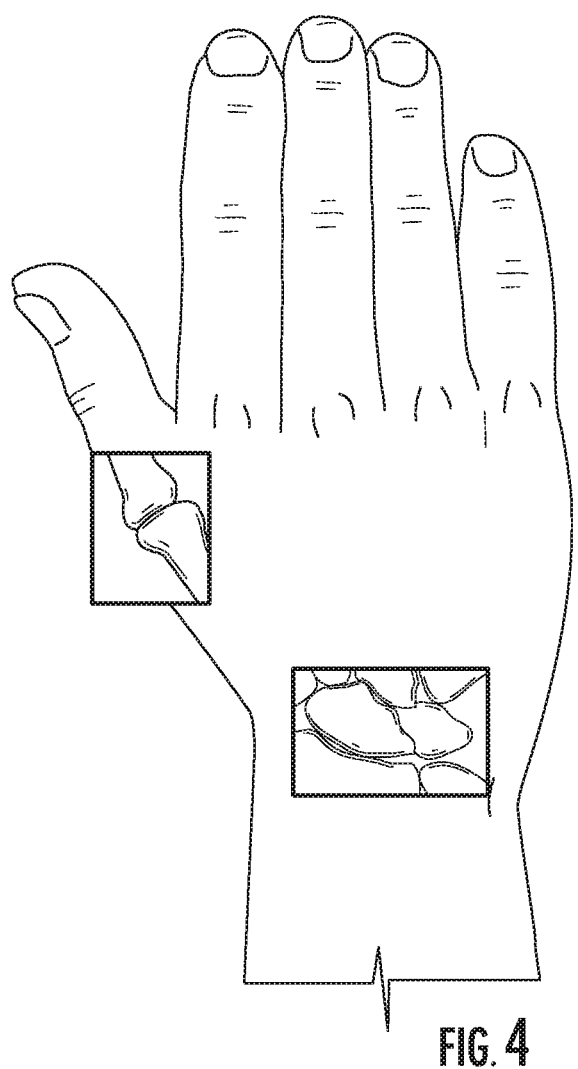
FIG. 4 is an illustration of the hand and wrist showing exemplary treatment sites according to embodiments of the present invention.
Figure 5:
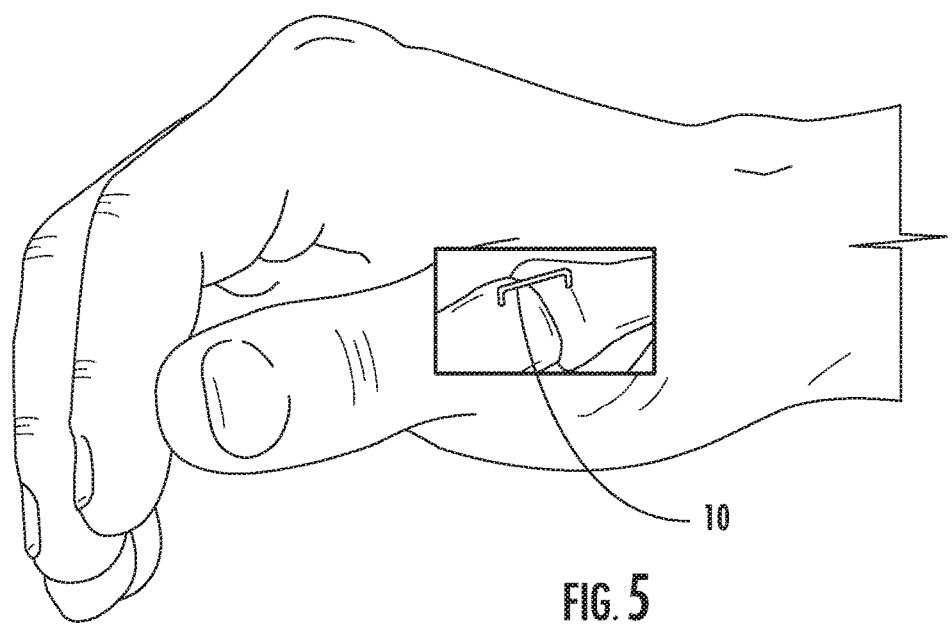
FIG. 5 is an illustration of a biostaple in position as a medial collateral ligament according to some embodiments of the present invention.
Figure 6:
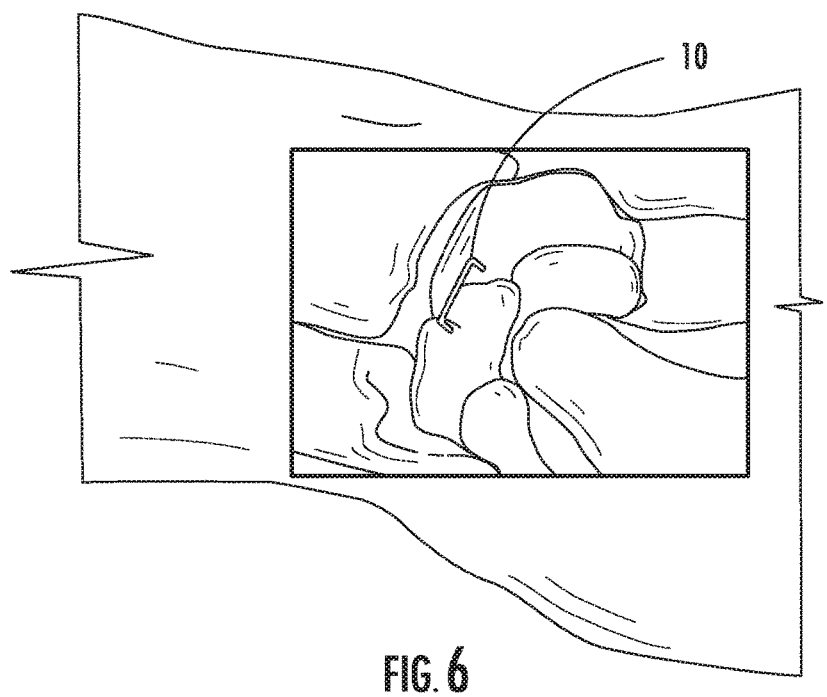
FIG. 6 is an illustration of a biostaple in position as a scapholunate ligament according to some embodiments of the present invention.

FIG. 4 illustrates exemplary hand and/or wrist treatment sites that may benefit from the use of biostaples 10. As will be recognized by those of skill in the art, the biostaple 10 may also be suitable for use in other locations as well (alone or with other devices). It is contemplated that the biostaple 10 will be particularly suitable for treatment of hand and/or wrist injuries of any ligament, such as, but not limited to, collateral ligaments. FIG. 5 illustrates a biostaple 10 with the end portions of legs 16, 17 in position in different local bones as a (medial ulnar) collateral ligament in a hand repair. FIG. 6 illustrates the biostaple 10 in position in the hand with one end of the biostaple in the lunate and the other in the scaphoid to form a scapholunate ligament. Although FIGS. 5 and 6 illustrate the treatment site using a single biostaple 10, two or more biostaples 10 may be used for a treatment. Where more than one biostaple 10 is used, they can be the same size and/or shape or different sizes and shapes.

Figure 7A:
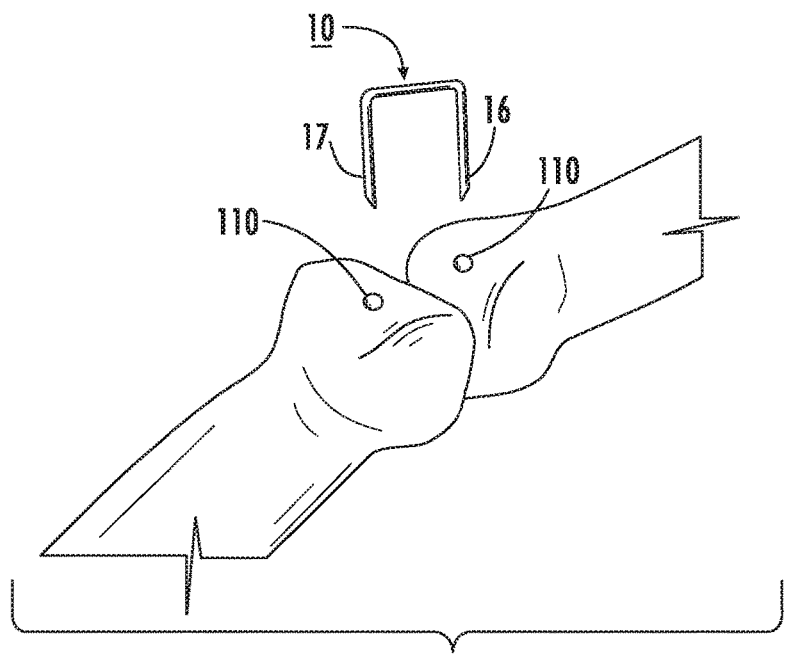
FIG. 7A is an exploded view of a biostaple aligned with bone tunnels according to embodiments of the present invention.
Figure 7B:
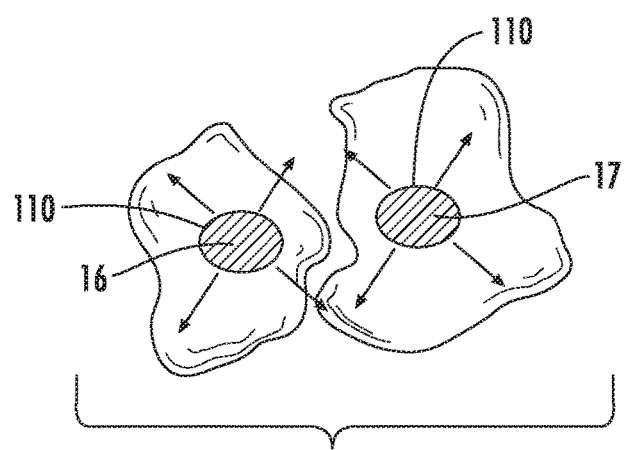
FIG. 7B is a cross-sectional view of the ends of the biostaple in the respective bone tunnel for hydraulic fixation according to embodiments of the present invention.

FIG. 7A illustrates two local bones with bone tunnels 110 formed therein sized with a tunnel depth and cross-sectional size to receive the end portions of respective legs 16, 17 of the biostaple 10. FIG. 7B illustrates that, in position, the legs 16, 17 occupy the entire cross-sectional space of the tunnels 110 and exert outward hydraulic fixation forces (shown by the arrows) onto the respective walls of the bone tunnels 110.

In some embodiments, the biostaples 10 can be placed in the bone tunnels 110 or other typically substantially rigid members with cavities or tunnels. When exposed to a hydrating environment, the biostaple 10 responds by increasing in cross-sectional area to fill and pressurize the bone tunnel, thereby providing an effective frictional restraint. The moisture-induced increase in size to cause the frictional restraint or engagement is referred to as "hydraulic fixation".

The bone tunnel(s) 110 that receives the legs 16, 17 may be substantially straight (vertical or horizontal). Alternatively, the tunnel 110 may angle depending on the target repair/implant site.

Figure 7C:
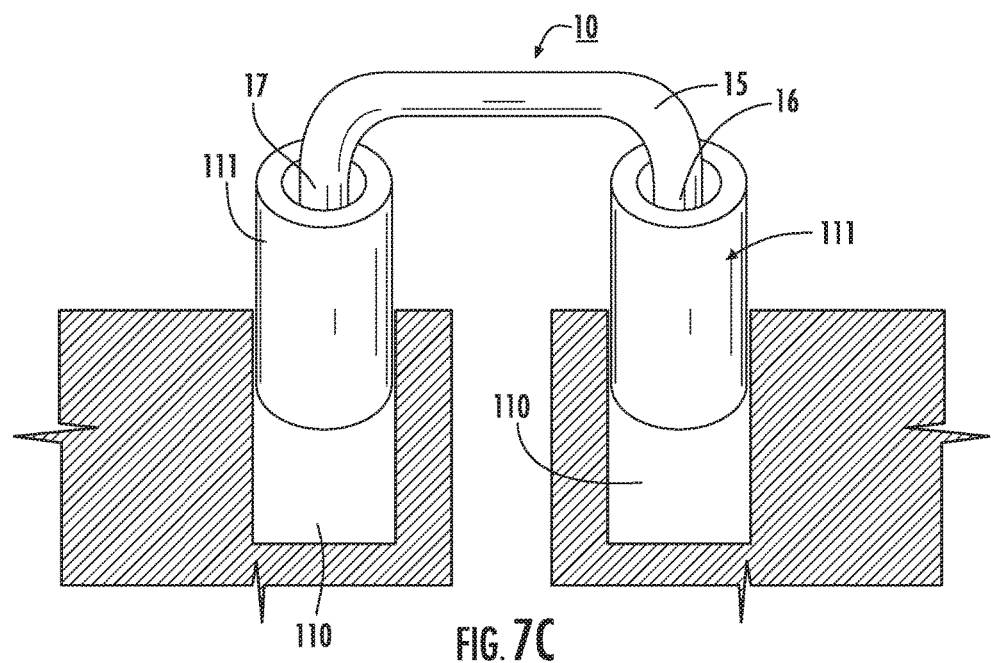
FIG. 7C is a greatly enlarged schematic illustration of a biostaple with its legs in corresponding sleeves for fixation in a bone tunnel according to some embodiments of the present invention.

FIG. 7C illustrates that the biostaple legs 16,17 (e.g., "tines") can be placed in a sleeve 111 of suitable material, such as, for example, allograft bone or any other suitable material, that can be used to seat the legs 16, 17 in a bone tunnel 110. The staple legs 16, 17 can be hydraulically and/or adhesively fixed within the bone sleeve 111. The sleeves 111 can be pre-drilled and labeled to identify which leg, 16 or 17 it is matched to for ease of installation, or provided as a blank and customized to size by a clinician. This configuration may allow for precise drilling of the bone sleeve to maximize or increase hydraulic fixation to a suitable level. This sleeve configuration may also provide more tolerance for the bone tunnel 110 diameter and/or can provide for compression fit of the sleeve.

Figure 7D:
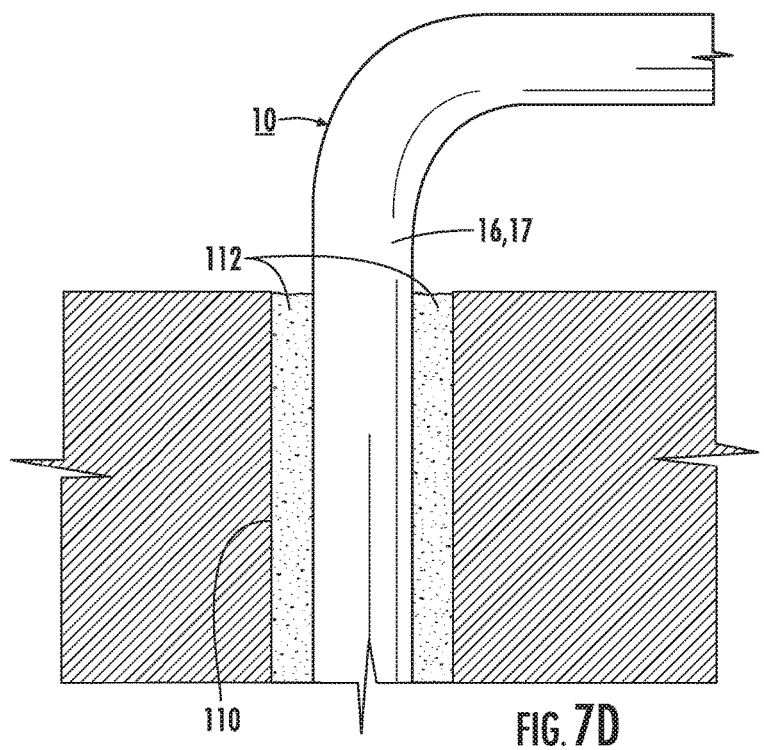
FIG. 7D is a greatly enlarged schematic illustration of a portion of a biostaple with its legs in fixation material (e.g., injectable bone cement) for fixation in a bone tunnel according to some embodiments of the present invention.

FIG. 7D illustrates that the staple legs (e.g., tines) can be placed in a bone tunnel 110 containing a biocompatible fixation material 112, such as an adhesive, bone paste or other suitable cement to aid in affixing the staple 10 in target bone. Examples of suitable fixation materials are calcium phosphate cements. This configuration allows a user to make the tunnel hole 110 fit the staple leg 16, 17 rather than the staple leg 16, 17 or tunnel path being correspondingly sized so as to provide the desired precise sizing for proper hydraulic fixation. A fast setting injectable bone cement can be used, such as, for example, Norian® from Norian Corporation having a place of business in West Chester, Pa., USA. The fixation material 112 can also be used with the sleeve 110 (inside and/or outside the sleeve).

The bone tunnels 110 can be blind and vary in width (diameter) and length depending on the target application. The length of the bone tunnels 110 is typically between about 3 mm to about 12 mm, more typically between about 6-9 mm. The bone tunnels 110 can have a diameter of between about 1.0-2.0 mm, typically between about 1.1 mm to about 1.4 mm and the legs 16, 17 can have a diameter that is substantially the same or slightly less (e.g., about 10% less) than the corresponding tunnel 110. The diameter of the bone tunnel 110 can be selected to substantially correspond to the diameter of the leg 16, 17 being inserted therein. Calipers can be used to measure each leg 16, 17 and select the drill bits to match the sizes. Each bone tunnel 110 may have a different size as each leg 16, 17 may vary slightly in size.

In some embodiments, the biostaple 10 is inserted in a dry or partially hydrated state and the interstitial fluid environment mediates a hydration process that proceeds until equilibrium is reached. The hydration causes an increase in the cross sectional area of the fibers, such as about 10%, until they fill the tunnel 110 and cause a build-up in internal pressure. The pressure causes a large frictional force, which effectively fixes the biostaple legs 16, 17 in the respective bone tunnel 110. The legs 16, 17 can be aligned with the respective bone tunnel 110 and pushed in. The beveled end of the legs can help facilitate equal forces are exerted during insertion. A driver or drill guide may also optionally be used to position the biostaple 10.

In some embodiments, the legs 16, 17 have a length of about 5-10 mm, typically at least about 7-8 mm for improved hydraulic fixation. In some particular embodiments, the crown 15 (also referred to as a bridge) can have a length that is shorter than the length of the legs 16, 17.

Figure 8:
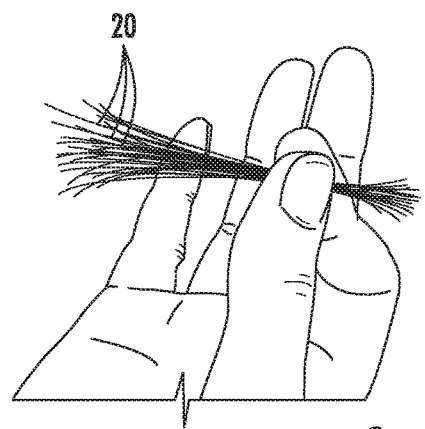
FIG. 8 is an illustration of exemplary fibers that can be used to form a biostaple according to embodiments of the present invention.
Figure 9:
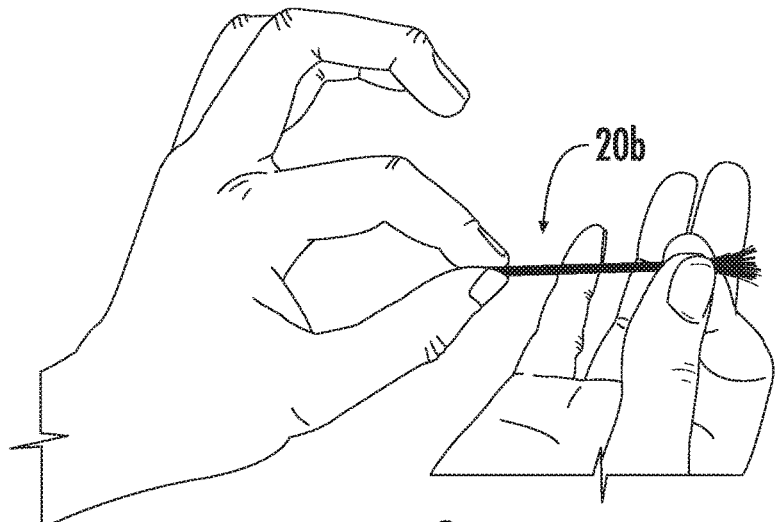
FIGS. 9 and 10 are illustrations of the fibers arranged into a bundle or array according to embodiments of the present invention.
Figure 10:
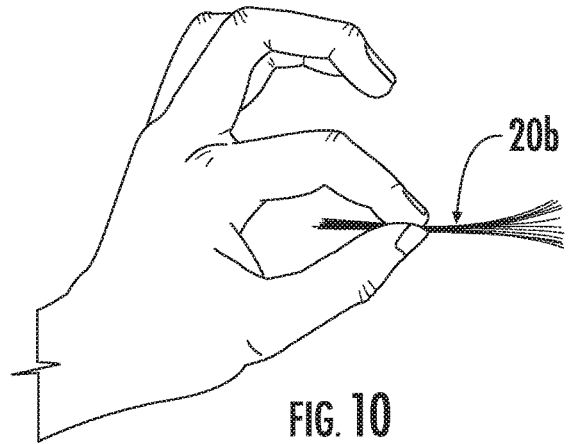

FIGS. 8-10 illustrate that the biostaple 10 can be formed using a plurality of discrete elongate fibers 20, typically NDGA treated collagen fibers. FIGS. 8 and 9 illustrate that the fibers 20 can be oriented to extend substantially longitudinally for a desired length and can be compressed together to form a bundle 20b of substantially parallel fibers 20. Although the fibers 20 are shown as having substantially the same length, some of the fibers 20 can have varying lengths but typically a plurality will have a length that is at least a major portion of a target length of the bundle 20b. The number of fibers 20 used can vary, but is typically between about 2-400, more typically between about 10-200 fibers, such as, for example between about 30-100 fibers. In some embodiments, the length of the bundle 20b is between about 3-20 cm, typically between about 5-10 cm, such as, for example, about 8.2 cm. However, it will be appreciated that these lengths are suitable for many hand and wrist applications, other lengths may be used for larger size applications.

Figure 11A:
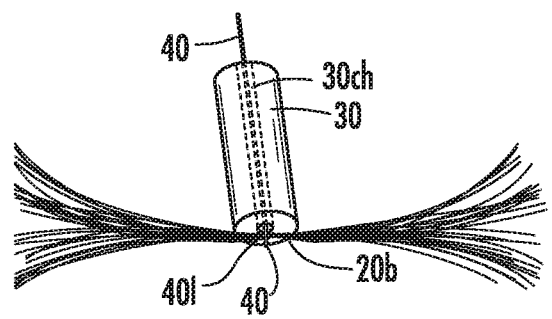
FIG. 11A is an illustration of a bundle of fibers captured in a looped portion of a thread for pulling through a fiber-forming holder according to embodiments of the present invention.
Figure 11B:
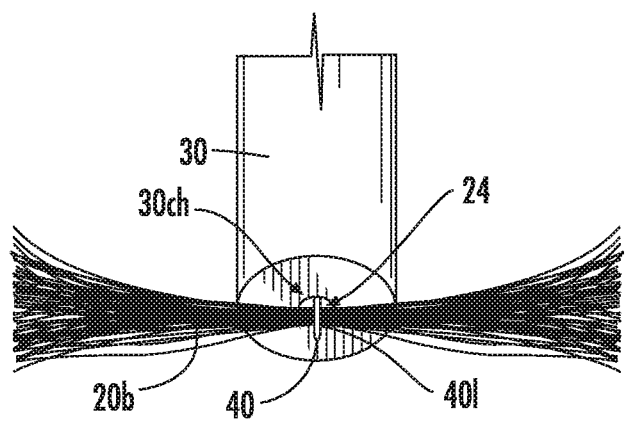
FIG. 11B is a greatly enlarged illustration of the bottom of the holder with the thread surrounding a medial portion of the fibers according to embodiments of the present invention.

FIGS. 11A and 11B illustrate a holding member 30 with a through channel 30ch with a thread leader 40 extending therethrough. The holding member 30 can be nylon or other material that has a low friction surface for ease of sliding. The lower portion of the thread 40 has a loop 40l that is sized to surround a portion of the fibers 20b. Thus, the bundle of fibers 20b can be captured by at a medial portion thereof by the thread 40 (e.g., held inside the loop of thread 40l). The thread and fibers 20 are then pulled through the channel or cavity 30ch. The bundle 20b grasped by the thread 40 defines a leading end portion or edge 24. Pulling the bundle 20b through the channel 30ch causes the opposing ends 21, 22 of the bundle 20b to fold together as shown in FIGS. 12A-12E. As shown, the folding of the fibers 20 together doubles the number of fibers used to form a biostaple. For example, where 38 discrete fibers are used, after folding in half a resulting biostaple will have about 76 fibers along substantially its entire length. The thread 40 can also be used to pull the fiber bundle 20b into a mold tunnel 50t (FIGS. 14B, 14C) to form the desired staple shape as will be discussed below.

Figure 13A:
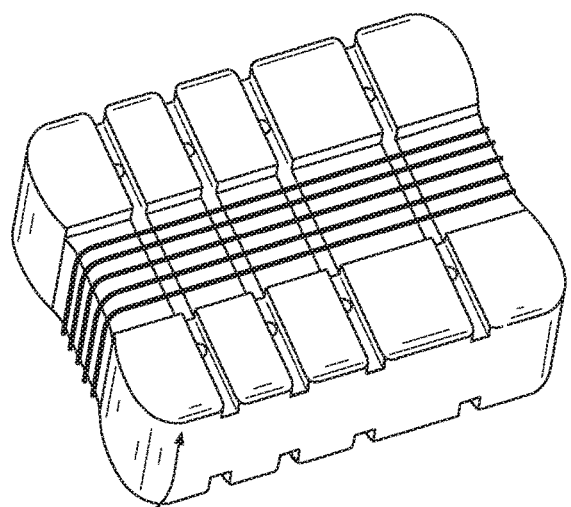
FIG. 13A is a top perspective view of a staple mold according to embodiments of the present invention.
Figure 13B:
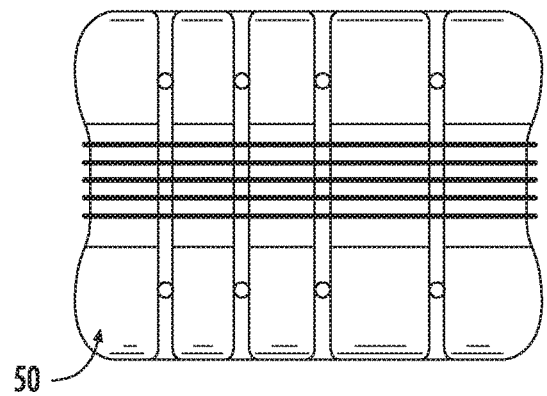
FIG. 13B is a top view of the mold shown in FIG. 13A.

FIGS. 13A and 13B illustrate one example of a biostaple mold 50. The mold 50 includes at least one mold tunnel 50t that is shaped to form the staple shape. The mold 50 can comprise TEFLON with the apertures forming the tunnels 50t acting as a vacuum plenum. The mold tunnel diameter can be between about 1.1-1.4 mm for some embodiments. As shown in FIGS. 14E and 14F, the mold 50 includes a plurality of mold tunnels 50t to concurrently hold a plurality of separate fiber bundles 20b for forming the staple shape. Each tunnel 50t has two spaced apart, substantially vertical tunnel portions $50v_1$ and $50v_2$ that receive the leading end portion of the fiber bundles 24 and the lower end portion 21, 22 of the fiber bundles to form the respective legs 16, 17 of the biostaple 10. As shown in FIG. 14E, a medial portion of the fiber bundle that extends between the end portions 24 and 21, 22 resides against an open surface channel formed in the exterior surface of the mold 50; this portion of the fiber bundle 20b forms the crown 15. As also shown in FIG. 14E, a series of cross-ties 55 can help hold the crown 15 against the mold body during processing. In other embodiments, the top mold surface 51 can include sides that partially close over the crown 15 to help hold the fibers in location (not shown). A cap or other retaining means can also be used.

Figure 14A:
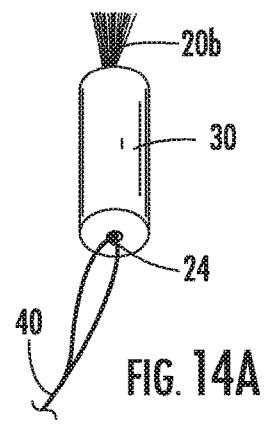
FIGS. 14A-14F are illustrations of a series of operations that can be used to pull the bundle of fibers through a tunnel in the mold shown in FIG. 13A to form a staple shape according to embodiments of the present invention.
Figure 14B:
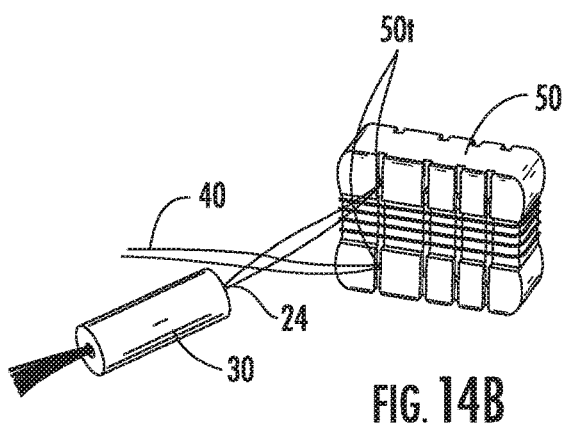
Figure 14C:
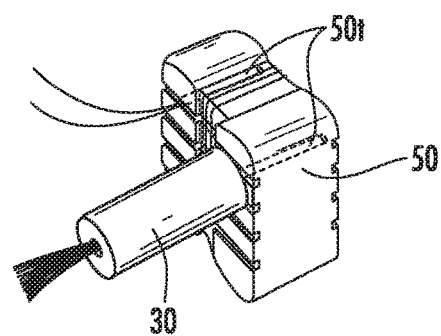
Figure 14D:
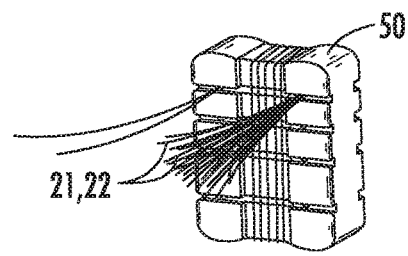
Figure 14E:
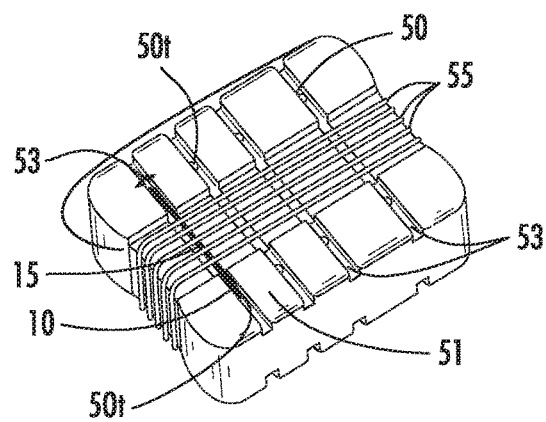
Figure 14F:
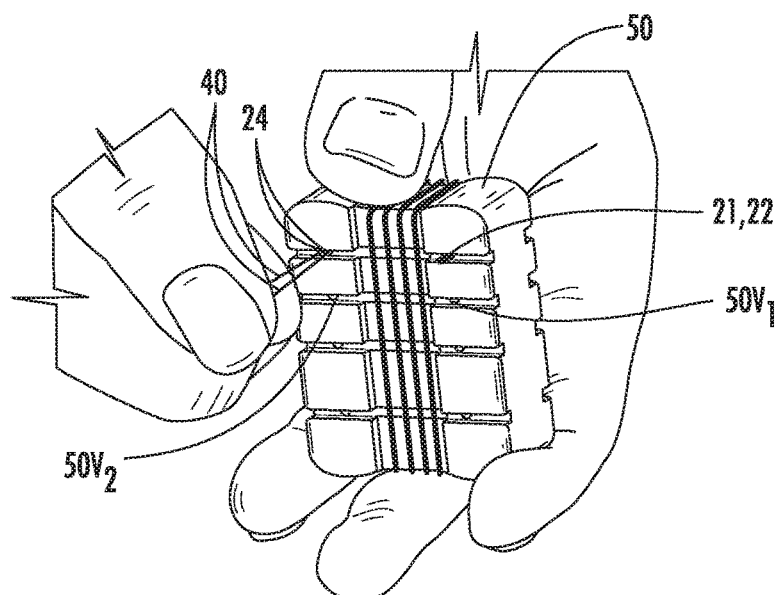

FIGS. 14A-14F illustrate a series of operations that can be used to position the fiber bundles 20b in the mold 50. As shown in FIG. 14A, the leading edge of the fiber bundle 24 is pulled out of the holding member 30 by thread 40. The leading end of the thread 40 is serially threaded through the vertical tunnels $50v_1$, $50v_2$, as shown in FIG. 14B. The holding member 30 is placed adjacent the entry location of the thread 40 into the mold tunnel 50t as the trailing edge of the thread 40 (e.g., the loop 40l) is pulled through the tunnel 50t. The leading edge of the fiber bundle 24 exits the holder 30 and enters the first vertical tunnel $50v_1$, travels across the open top channel 53, then into and through the second vertical tunnel $50v_2$. As shown in FIG. 14F, the fiber bundle 20b is then positioned in the mold tunnel with the folded/leading edge of the fibers 24 on one side of the mold tunnel $50v_2$ and the other end portions 21, 22 at the end of the other tunnel $50v_1$.

Although shown as one discrete fiber bundle forming one staple 10, it will be appreciated that one continuous length of fiber bundle 20b can be used to form a plurality of staples by threading them through one or more other tunnel 50t in the mold, then separating before or after further processing.

While the holding member 30 is shown as tubular, other shaped members may also be used. Also, in some embodiments, the fibers 20 are not required to be folded together before introduced into a mold to form the geometric shape of the biostaple. For example, the thread or a needle (not shown) in communication with the fibers 20b can be used to lead the fiber bundle 20b into the mold tunnel. Also, other means of inserting the bundle of discrete fibers into a mold tunnel may also be used. For example, a gel, adhesive, a flexible sleeve or the like can be formed or placed on an end portion of the fiber bundle 20b to compress the fibers together so that they can be more easily inserted and/or guided into/through a mold tunnel (not shown).

Figure 13C:
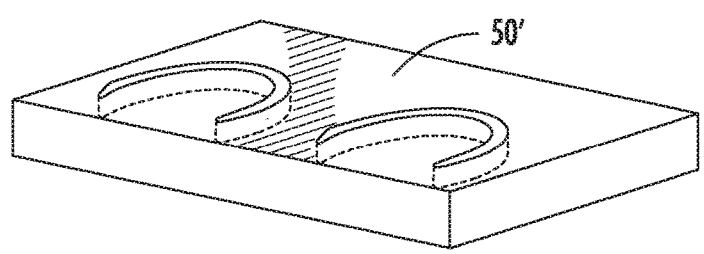
FIG. 13C is a top perspective view of a mold according to embodiments of the present invention.

As shown in FIG. 13C (last sheet of figures), in yet other embodiments, the mold 50' can have an open curvilinear cavity 50c and the fibers 20b can be placed into a shallow open curvilinear cavity 50c to form the desired staple shape. A restraining member(s) can be placed over the fiber bundles 20b to hold them in the cavity during exposure to subsequent processing to form the staple shape, such as, for example, exposure to a stiffening or solidifying substance and/or polymerization. The mold cavity channels 30c may include drain/through apertures to allow liquid to be drawn around the fiber bundles 20b during processing.

FIG. 15 illustrates that after loading the mold 50, the fiber bundles 20b held in the mold 50 can be placed in a liquid bath 70. The liquid bath 70 can comprise a gelatin solution at a desired temperature (e.g., between about 35-40 degrees C., typically about 37 degrees C.), such as, for example, an aqueous solution of between about 5-30% gelatin, typically about 9-15% gelatin, and more typically about 10% gelatin. The gelatin can be any suitable biocompatible gelatin, such as, for example, purified collagen gelatin or porcine gelatin. The gelatin may be NDGA treated gelatin. FIG. 16 illustrates that the mold 50 in the liquid bath 70 can be placed in a vacuum chamber 100 in communication with a vacuum pump 100p for vacuum infiltration of the fibers with the gelatin (the system can also alternately be configured so that the liquid bath resides in the chamber before the mold is placed therein). The infiltration process can be carried out at any suitable vacuum, such as, for example, at a vacuum of about 60 cm Hg, for about 5 minutes. The vacuum chamber can be at room temperature (though the mold is typically placed in heated liquid bath (e.g., about a 37 degree gelatin bath) then placed in the vacuum chamber, which can be at room temperature). Other pressurized infiltration systems can be used, such as, for example, pressure chambers or injection systems to expose the fiber bundles to the gelatin solution. As shown, the mold 50 is placed with the legs 16, 17 up but the mold may be held in other orientations as well, directly on the bottom surface of the liquid bath container or on a spacer, shelf or other member.

FIG. 17 illustrates that the fiber bundles 20b can be allowed to dry in the mold, air dry or actively dry such as by placing in an oven, blowing air and the like. The mold with staples can be again exposed to the liquid bath of gelatin in the vacuum system to reinfiltrate the gelatin to fill substantially all voids to bind fibers for a substantially constant diameter. The gelatin can be an NDGA-treated gelatin.

After a desired number of vacuum infiltration and drying cycles, the biostaples 10 can be removed from the mold 50 with the staple retaining the desired molded shape. The biostaple 10 can then be NDGA cross-linked and ethanol washed and dried. The beveled, sharp and/or tapered edges 18 can be cut or otherwise formed in the ends of the legs 16, 17 after removal from the mold 50.

Figure 18:
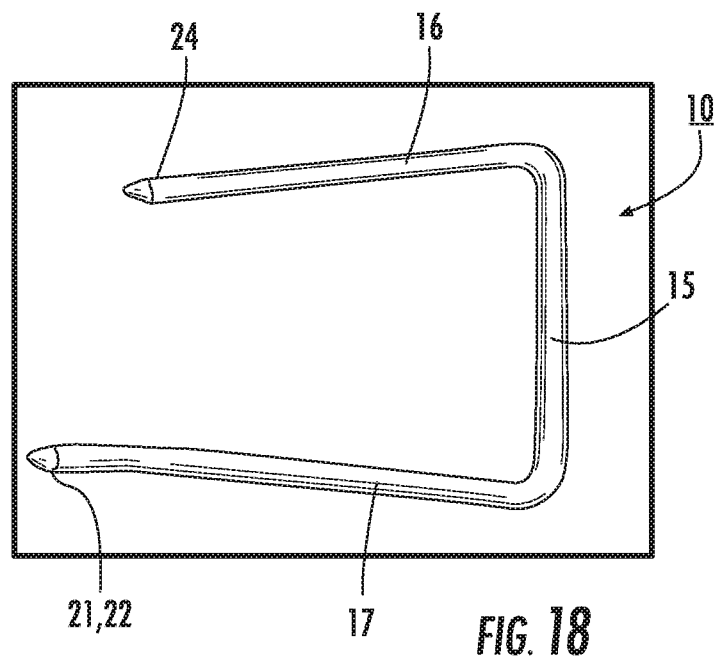
FIG. 18 is a digital image of a collagen fiber staple according to embodiments of the present invention.
Figure 19:
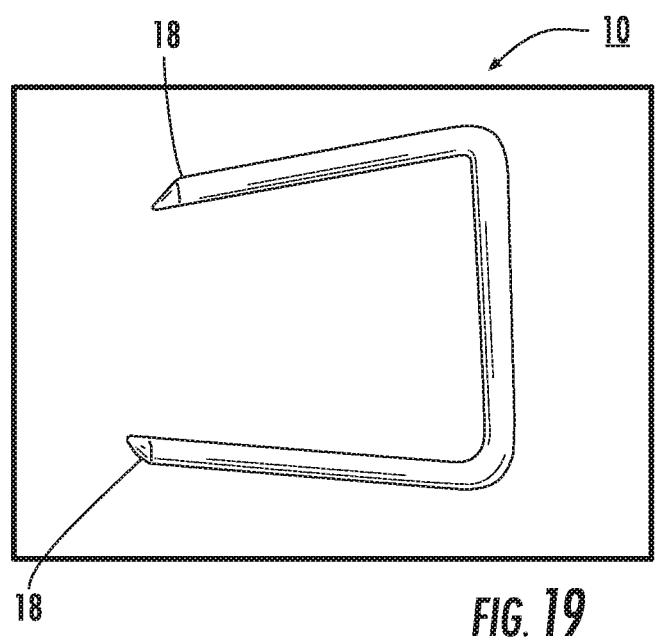
FIG. 19 is a digital image of the staple shown in FIG. 18 with the ends of the legs cut to define a taper with a leading end point for easier insertion into bone tunnels according to embodiments of the present invention.

FIGS. 18 and 19 are digital photographs of prototypes of the biostaples 10. FIG. 18 illustrates the shape of the prototype upon removal from the mold. FIG. 19 illustrates the prototype after the ends have been cut for the taper 18.

In particular embodiments, the array or bundles of fibers 20b may also optionally comprise braided segments, for example, a portion of the crown 15 (not shown). The term "braided" and derivatives thereof mean to (inter)weave and/or interlock, in any manner, three or more fibers or bundles of fibers together, including knitting and knotting and combinations of these or other interlocking constructions.

The biostaple 10 can be configured to be sufficiently rigid to retain its shape yet also flexible to approximate the stiffness and flexibility of a ligament. Alternatively, the biostaple 10 may be substantially rigid or have increased rigidity in situ (typically with more fibers increase rigidity).

Figure 12A:
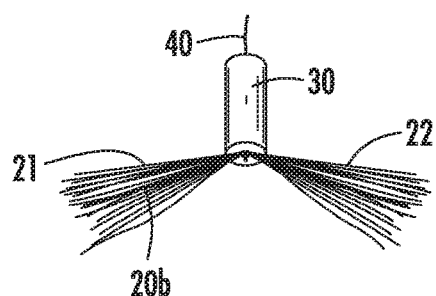
FIGS. 12A-12E are illustrations of a series of operations to pull the bundle of fibers through a channel or tunnel in the holder to force the opposing end portions of the fibers together according to embodiments of the present invention.
Figure 12B:
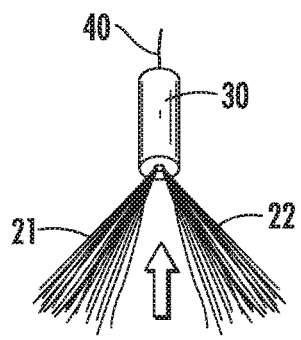
Figure 12C:
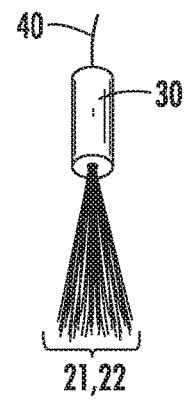
Figure 12D:
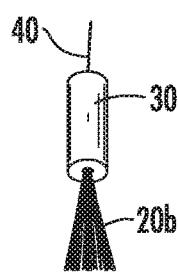
Figure 12E:
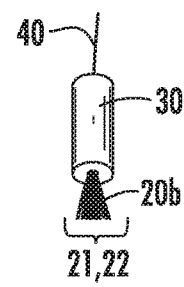

As shown in FIGS. 11A and 12E, the multiple fibers 20 can be axially arranged so that at least a majority of the fibers are substantially parallel to each other over at least a major portion of the length of the construct 10, typically over substantially the entire length of the construct 10. Some of the fibers may not run the entire length of the biostaple construct 10.

In typical embodiments, the overall length "L" of the biostaple 10 (measured from end to end) is substantially constant between the dry or partially hydrated and hydrated configurations, typically changing less than about 3%.

In some embodiments, the cross-sectional area of the legs 16, 17 is sized to be between about 60%-99% of that of the bone tunnel 110 at insertion, typically between about 80%-99%. Measured outside the body, after 24 hours in a saline bath at ambient conditions, the biostaple 10 can be configured to expand to an increased hydrated unconstrained equilibrium cross-sectional area of between about 10% to about 250%, typically between about 50-220%.

The biostaple 10 can be a relatively tightly compressed array of fibers providing the desired mechanical properties and configuration and, in some embodiments, can allow for neo-tissue in-growth.

The biostaple 10 and/or fibers 20 can incorporate anti-inflammatory agents or other pharmaceutically suitable agents. The biostaple 10 can be configured with an anti-swelling inhibitor to control the time or rate of hydration induced-swelling to allow enough time for a clinician to properly orient and adjust the legs 16, 17 in situ. For example, the anti-swelling inhibitor may be a heat or light sensitive coating or matrix and/or hydrogel coating or matrix that can dissolve or resorb when in the body over a relatively short period (such as to allow the swelling to occur about 20-60 minutes after placement). In some embodiments, natural body heat may be sufficient to release the coating and initiate the swelling or a clinician may locally apply increased heat. Other swelling-inhibitor removal techniques may be used depending on the inhibitor, such as, for example, applying laser or infrared light, RF heat, heated and/or solvent liquid or fluid irrigation materials, and the like, to release the swelling inhibitor to allow the hydration-induced swelling. The swelling-inhibitor may also be lubricious so as to facilitate slidable insertion as appropriate.

The biostaple 10 may also or alternatively be coated or impregnated with a thin film of polylactic acid (PLA) or other suitable substance to promote strength and/or ease of handling. For example, the biostaple 10 can be dipped, painted or sprayed with a 3% solution of PLA in chloroform or other suitable solution.

The fibers 20 may comprise NDGA polymerized collagen fibers. The biostaple 10 can have between about 2-400 fibers. In particular embodiments, the collagen fibers can have an average fiber width (diameter) of between about 0.01 mm to about 0.10 mm, typically between about 0.1 and 0.5 mm. The fibers 20 can be derived from any suitable source, see, e.g., co-pending U.S. patent application Ser. No. 11/964,756, the contents of which are hereby incorporated by reference as if recited in full herein. The length of the biostaple can be substantially constant (during the insertion step and after the legs expand in situ to engage the wall of the bone tunnel. Also, biostaple can optionally include (e.g., be coated, impregnated and/or amalgamated with) a gel or other material. The coating may be to promote fibroblasts, and/or may comprise one or more of an anti-inflammatory agent, an antibiotic or other therapeutic agent.

Figure 20:
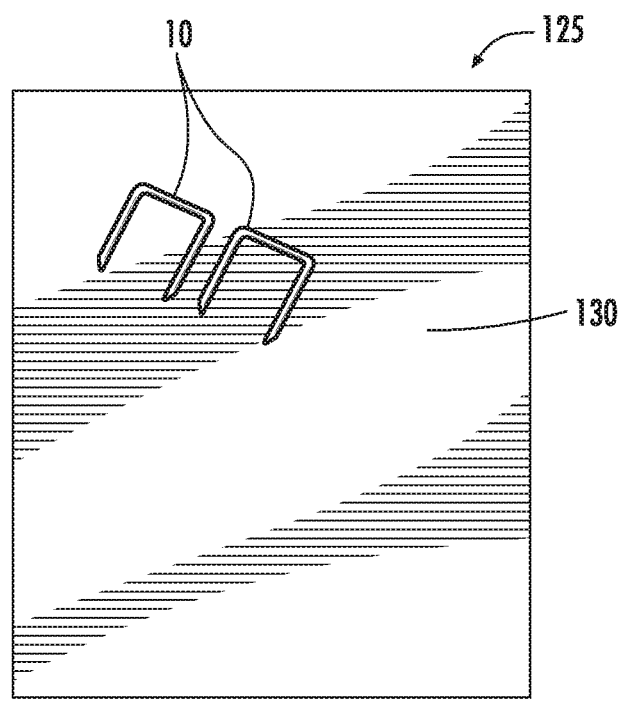
FIG. 20 is a schematic illustration of a medical kit according to embodiments of the present invention.

FIG. 20 is a schematic illustration of a medical kit 125 that includes at least one biostaple 10, shown as including at least two for the clinician to use one or two or to select one for use. The biostaples can also be provided in different size ranges (different crown widths and/or leg lengths). The biostaple 10 can be held in a sealant 130 that holds the biostaple(s) 10 in a dry or partially hydrated state. The sealant package 130 may optionally include a desiccant to help maintain the desired dry or partially hydrated state of the biostaple 10. The sealant 130 may be a flexible, sealed sterile bag that is substantially impermeable at normal atmospheric conditions. The kit 125 may optionally include a driver and/or drill bits to slidably insert the construct in position in the bone tunnel 110 and/or form the desired bone tunnel size.

The biostaple 10 can be configured to have a strength and stiffness similar to natural ligament and can provide an effective scaffold for neo-tendon and ligament to grow into and further enhance some repairs. The kit 125 may include a temperature warning so that the biostaple 10 is not exposed to unduly hot temperatures that may degrade the implant. A temperature sensor may optionally be included on the package of the kit (not shown) to alert the clinician as to any excessive or undue temperature exposure prior to implantation.

Although described herein as collagen fibers, the fibers 10 can be any biologically compatible fibers formed in any suitable manner that can function as a biostaple. The biostaple 10 is suitable for chronic implantation and may optionally be absorbed, resorbed and/or biodegradable over time.

As noted above, the fibers 20 can comprise collagen fibers such as glutaraldehyde cross-linked collagen fibers and/or NDGA-treated collagen. Suitable ways of forming NDGA polymerized and/or treated fibers are described in U.S. Pat. Nos. 6,565,960 and 6,821,530, the contents of which are hereby incorporated by reference as if recited in full herein. Generally stated, bulk collagen can be solubilized by digestion with a protease, then extruded into a synthetic fiber. Properly processed NDGA polymerized fibers are biocompatible. After the polymerization process, the fibers can be washed in ethanol and phosphate buffered saline to remove cytotoxins due to leachable reaction products.

NDGA-treated collagen fibers are biocompatible and have desirable mechanical properties. For additional discussion of the NDGA polymerized fibers, see, Thomas J. Koob, *Biomimetic approaches to Tendon Repair*, Comparative Biochemistry and Physiology Part A 133 (2002) 1171-1192. See also, co-pending U.S. Provisional Application Ser. No. 60/883,408, Filed Jan. 4, 2007 to Koob et al., entitled, *Methods of Making High Strength NDGA Polymerized Collagen Fibers and Related Collagen-Prep Methods, Medical Devices and Constructs*, the contents of which are hereby incorporated by reference as if recited in full herein.

It is contemplated that the rate of hydration in the bone tunnel may be controlled for some applications to allow sufficient time for surgical placement of a bioprosthesis and, if needed, adjustment of length and tension. The amount of time after the fibers are exposed to a hydrating environment and the speed of fixation can be coordinated so as to avoid premature locking. A means of fast insertion and/or controlling the rate of hydraulic swelling in vivo may be used, for example, hydrogel matrices are potential hydration retardants.

Another advantage of the swelling properties of the fiber constructs is that swelling occurs substantially only perpendicular to the long axis of the fiber. The constructs do not substantially lengthen or shorten. Applying the proper tension in the re-attachment of tendons or ligaments to bone would not suffer from problematic lengthening of the construct due to hydration.

NDGA-polymerized collagen fibers may be particularly suitable for implementing the hydraulic fixation. They can provide the swelling properties for effective hydraulic fixation, they are not cytotoxic, they do not harbor diffusible cytotoxic reaction products, they are biocompatible with cells in vitro, and they are biocompatible and can be configured so that they do not get degraded for six weeks in vivo. See, Koob, *Biomimetic approaches to tendon repair*, Comp. Biochem. Physiol. A Mol. Integr. Phys. 133: 1171-1192 (2002). The biocompatibility of these fibers combined with biomechanics similar to natural tendon and ligament offer a potential of serving as effective scaffolding for new tissue growth.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. An implantable biostaple comprising:
   a body including a crown and two opposing outwardly extending legs with the crown bridging between the legs, wherein ex vivo the body is a self-supported substantially U-shaped body,
   wherein the biostaple has at least one bundle of collagen fibers comprising about 2 to about 400 elongate collagen fibers that extend across the crown and over a length of each of the legs, and
   wherein a majority of the elongate collagen fibers are substantially parallel to each other over at least a major portion of the length of the biostaple.

2. The implantable biostaple of claim 1, wherein the two opposing outwardly extending legs expand in situ after implantation to frictionally engage a bone tunnel wall or sleeve to thereby affix the biostaple in the bone tunnel.

3. The implantable biostaple of claim 1, wherein the biostaple is dry or partially hydrated at implantation.

4. The implantable biostaple of claim 1, wherein the two opposing outwardly extending legs are sized to reside in a bone tunnel that is between about 5-10 mm long.

5. The implantable biostaple of claim 1, wherein, in a fully hydrated unconstrained state, when measured ex vivo, the biostaple increases in cross-sectional area, on average, at least about 10%, and has a substantially constant length relative to a dry or partially hydrated state.

6. The implantable biostaple of claim 1, wherein the biostaple is an implant for a collateral ligament for the hand or wrist.

7. The implantable biostaple of claim 1, wherein the biostaple is an implant for a medial ulnar collateral ligament.

8. The implantable biostaple of claim 1, wherein the biostaple is an implant for a scapholunate ligament.

9. The implantable biostaple of claim 1, wherein each of the two opposing outwardly extending legs has an end portion with a leading beveled edge, and wherein at least a portion of each leg expands after implantation in a direction that is substantially orthogonal to an axial direction of the fibers in vivo to frictionally engage a sleeve or a wall of a bone tunnel of a patient.

10. The implantable biostaple of claim 1, wherein the elongate collagen fibers are NDGA polymerized collagen fibers.

11. The implantable biostaple of claim 1, wherein the at least one bundle of collagen fibers comprises about 10 to about 200 elongate collagen fibers.

* * * * *